(12) United States Patent
Chin et al.

(10) Patent No.: US 10,543,073 B2
(45) Date of Patent: Jan. 28, 2020

(54) SYSTEM AND METHODS FOR CLOSING A FASCIAL OPENING

(71) Applicants: Albert K Chin, Palo Alto, CA (US); Thomas A. Kramer, San Carlos, CA (US)

(72) Inventors: Albert K Chin, Palo Alto, CA (US); Thomas A. Kramer, San Carlos, CA (US)

(73) Assignee: TAS Medical Inc., San Carlos, CA (US)

( * ) Notice: Subject to any disclaimer, the term of this patent is extended or adjusted under 35 U.S.C. 154(b) by 100 days.

(21) Appl. No.: 15/802,396

(22) Filed: Nov. 2, 2017

(65) Prior Publication Data

US 2018/0116778 A1    May 3, 2018

Related U.S. Application Data

(60) Provisional application No. 62/416,655, filed on Nov. 2, 2016.

(51) Int. Cl.
*A61B 17/02* (2006.01)
*A61F 2/00* (2006.01)
*A61B 17/00* (2006.01)

(52) U.S. Cl.
CPC ........ *A61F 2/0063* (2013.01); *A61B 17/0218* (2013.01); *A61B 2017/00407* (2013.01); *A61B 2017/00818* (2013.01); *A61B 2017/00862* (2013.01); *A61B 2017/0225* (2013.01); *A61F 2002/0072* (2013.01); *A61F 2220/0008* (2013.01); *A61F 2220/0091* (2013.01)

(58) Field of Classification Search
CPC ............ A61B 17/0401; A61B 17/0482; A61B 17/0485; A61B 2017/06052; A61B 17/82; A61B 17/842
USPC .................................... 600/208; 606/74, 148
See application file for complete search history.

(56) References Cited

U.S. PATENT DOCUMENTS

| 9,451,953 B2 | 9/2016 | Sengun | |
| 2013/0165955 A1* | 6/2013 | Chin | ...................... A61B 17/06 606/148 |
| 2017/0325802 A1 | 11/2017 | Bennett et al. | |

FOREIGN PATENT DOCUMENTS

FR    2438464 A1    5/1980

* cited by examiner

*Primary Examiner* — Si Ming Ku
(74) *Attorney, Agent, or Firm* — Craig M. Litherland

(57) ABSTRACT

A system and method for closing a fascial opening is disclosed. The system may include a strap that may be locked into each of a pair of anchors placed anterior to a muscle and on opposite sides of a fascial opening, one or more delivery tubes for delivering the anchors, and a needle for pulling the strap into each anchor. The method may include the steps of placing a dilating port through a skin incision, inserting an anchor through the dilating port, placing a strap into the body cavity, whereupon the strap may be pulled through the anchor. A second anchor may be placed on the contralateral side of the defect so that the strap may be pulled through the second anchor and cinched tightly closing the defect. The anchors may have a locking aperture that engages with the strap.

2 Claims, 21 Drawing Sheets

SYSTEM AND METHODS FOR CLOSING A FASCIAL OPENING

RELATED APPLICATIONS

The present application claims priority to U.S. Provisional Patent Application No. 62/416,655, the entirety of which is incorporated herein by reference.

TECHNICAL FIELD

This disclosure relates to medical devices and methods, and more specifically to systems and methods for tissue approximation and fixation.

BACKGROUND

Ventral hernias are abdominal wall defects that generally occur following a breakdown in the closure of a previous abdominal open surgical midline incision. 350,000-500,000 ventral hernias are repaired annually in the United States. Ventral hernias may be greater than 10 cm wide and 40 cm or more in length and extend below the xiphoid process of the sternum inferiorly to the pubic symphysis; they may be repaired via conventional "open" methods requiring a large incision, or laparoscopic procedures requiring small abdominal incisions.

Ventral hernias may arise after a patient undergoes abdominal surgery. For example, upon completion of an open abdominal surgical procedure, closure of the full thickness abdominal wall is performed. Interrupted sutures are placed through the anterior rectus sheath, the rectus muscle, and the posterior rectus sheath. Suture repair has a long-term failure rate of 41%-52%, leading to ventral hernia formation. Poor tissue strength coupled with significant tension in the suture lines leads to failure of the abdominal closure requiring hernia repair. In conventional laparoscopic repair, multiple trocar ports are inserted to place a large patch of prosthetic mesh to cover the defect. This approach causes far less postoperative pain as compared to open methods because a large abdominal incision is avoided. However, the abdominal defect is generally not closed; rather, the large prosthetic patch is tacked onto the inner surface of the abdominal wall to cover the defect. Placement of a large piece of artificial material results in a high rate of postoperative complications, including seroma formation. The fluid loculation of the seroma then increases the potential for infection of the laparoscopically placed mesh, necessitating its removal plus antibiotic therapy. Bowel adhesions are also a potential complication due to the implantation of a large foreign body patch.

It is desirable to close the abdominal defect using a laparoscopic technique, either partially or completely, to significantly decrease the size of the prosthetic mesh patch needed to repair the ventral hernia or eliminate the use of a mesh patch entirely at the discretion of the surgeon. U.S. Pat. No. 9,055,940 describes a system and technique that uses capture devices that puncture through the abdominal wall on both sides of the hernia defect and grasp the ends of a suture delivered into the abdominal cavity. One end of the suture is pulled out of the body, and a trapping device is tunneled subcutaneously from the first end of the suture to grasp and deliver the opposite end of the suture to the first puncture site. The suture may be tied at the first puncture site, and the knot inserted through the skin down to the level of the anterior rectus sheath, where it may be tensioned to close the hernia defect.

The technique illustrated in U.S. Pat. No. 9,055,940 is repeated for each interrupted suture placed during ventral hernia closure. If a relatively close spacing of 2 cm is used between sutures to increase the strength of the repair, and a 30 cm long hernia defect is being closed, 14 interrupted sutures will be required. With wide defects, the sutures must be tensioned incrementally and sequentially to gradually reappose the edges, otherwise, the suture may tear through the abdominal wall tissue. A slip knot composed of two half-hitches is used to allow sequential tensioning of an individual suture. Continuous tension must be maintained on all sutures during the cinching and closure process. This may be performed by applying a surgical clamp immediately proximal to each slip knot after each sequential tensioning step. However, this leads to an excessive number of surgical clamps on the operating field.

The aforementioned hernia defect closure technique is overly tedious. Placement of each interrupted suture involves the following steps: (1) Insert suture loop into the abdominal cavity; (2) Insert suture capture device through abdominal wall and capture one end of suture; (3) Pull captured suture end out of the patient; (3) Insert suture capture device through opposite side of abdominal wall and capture opposite end of suture; (4) Insert trapping device through first puncture site and tunnel to engage the suture capture device on opposite side of abdominal wall; (5) Remove suture capture device to pull the opposite end of the suture out of the patient; (6) Pull the trapping device out of the patient so both ends of the suture loop exit one abdominal puncture site; (7) Tie two half-hitches in the suture to form a slip knot; (8) Push slip knot down to the anterior rectus sheath using a knot pusher; (9) Clamp the suture near the knot to maintain tension in the suture loop; (10) Serially tension all placed suture loops to bring the edges of the hernia defect together; (11) Tie multiple square knots and use the knot pusher to push each knot down to the level of the anterior rectus sheath to fixate each interrupted suture loop; (12) Cut excess suture from each knot. Hence, at least twelve surgical manipulation steps must be performed for each of the ten or more sutures placed in the patient.

The anchor device of Surti (U.S. Pat. No. 9,339,265) discloses an anchor delivery tool wherein the tissue anchor lies within the bore of a needle. As the outer diameter of the needle is larger than the diameter of the anchor, there exists potential for an anchor under continuous tension to dilate the relatively large tract in the muscle formed by needle insertion, leading to pullout of the anchor through the dilated tract. This scenario may be observed particularly in the weakened or attenuated tissue encountered in ventral hernia patients.

A laparoscopic technique and instrumentation is desired to place multiple interrupted fastening loops on each side of a hernia defect, maintain tension in each loop, and allow serial cinching of each loop to reappose the edges of the defect while preventing the sutures from incising, pulling out, or tearing through the muscle tissue.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

A system and method for closing a fascial opening are described herein. While the present disclosure describes the system and method in the context of hernia repair, and in particular ventral hernia repair, the devices and methods presently disclosed may be used in any surgical procedure for joining tissue, closing a tissue opening, or fastening a device to or between two or more sections of tissue. In the patient's midline, the left and right anterior rectus sheaths come together to form a single layer called the linea alba. A ventral hernia defect may be an opening in this layer. It may also be an opening that extends through the posterior rectus sheath, rectus muscle, and anterior rectus sheath; or it may be an opening in the fascia lateral to the rectus muscle. Additionally, while the current disclosure describes systems and methods in the context of laparoscopic surgery, the system and method may be applied to any other class of procedure such as open surgery or laparotomy, or robotic surgery.

Figure 1:
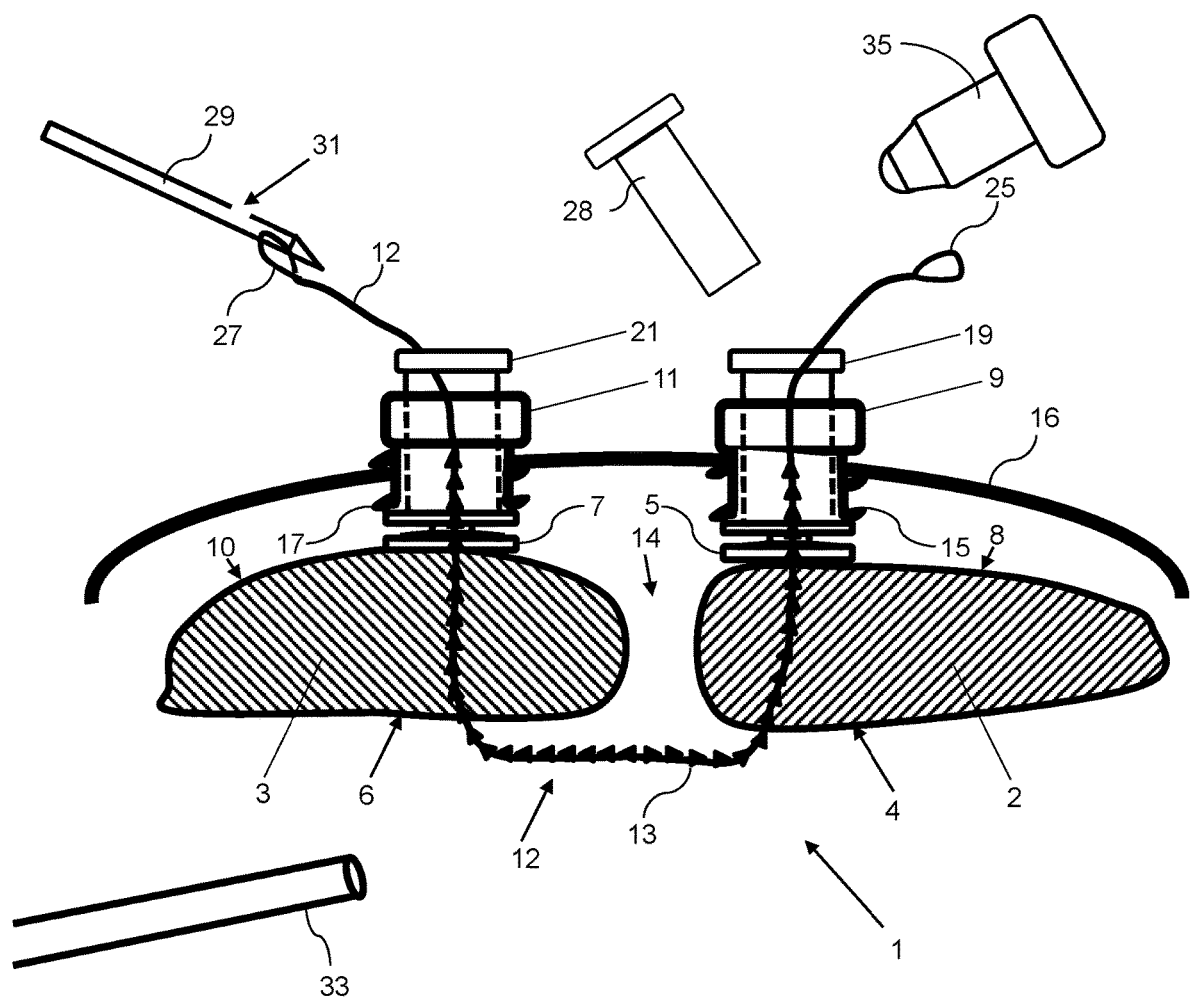
FIG. 1 depicts a system for closing a facial opening.

With reference to FIG. 1, a first exemplar embodiment of a system 1 for closing a fascial opening (e.g. ventral hernia) is shown and illustrated in the context of a cross section of the human body, i.e. during a surgical procedure. The system 1 may include by way of non-limiting example, one or more of the following: anchors 5 and 7, dilating ports 9 and 11, delivery tubes 19 and 21, a strap 12, an obturator 35, an anchor delivery plunger 28, and strap introducer 33. The anchors, 5 and 7, are shown in a deployed configuration and reside adjacent to the right and left anterior rectus sheaths 8 and 10, while the dilating ports 9 and 11 protrude through the skin and above the expanded anchors 5 and 7. The delivery tubes 19 and 21 sit within their respective dilating ports 9 and 11. In the phase of the procedure illustrated in FIG. 1, the strap 12 protrudes through the left and right posterior rectus sheaths 4 and 6, the right and left rectus abdominus muscles 2 and 3, the right and left anterior rectus sheaths 7 and 8, the anchors 5 and 7, as well as through the delivery tubes 19 and 21, which are housed in the dilating ports 9 and 11. FIG. 1 shows this exemplar system 1 in the midst of a surgical procedure, the details of which are further described in this disclosure.

Figure 2A:
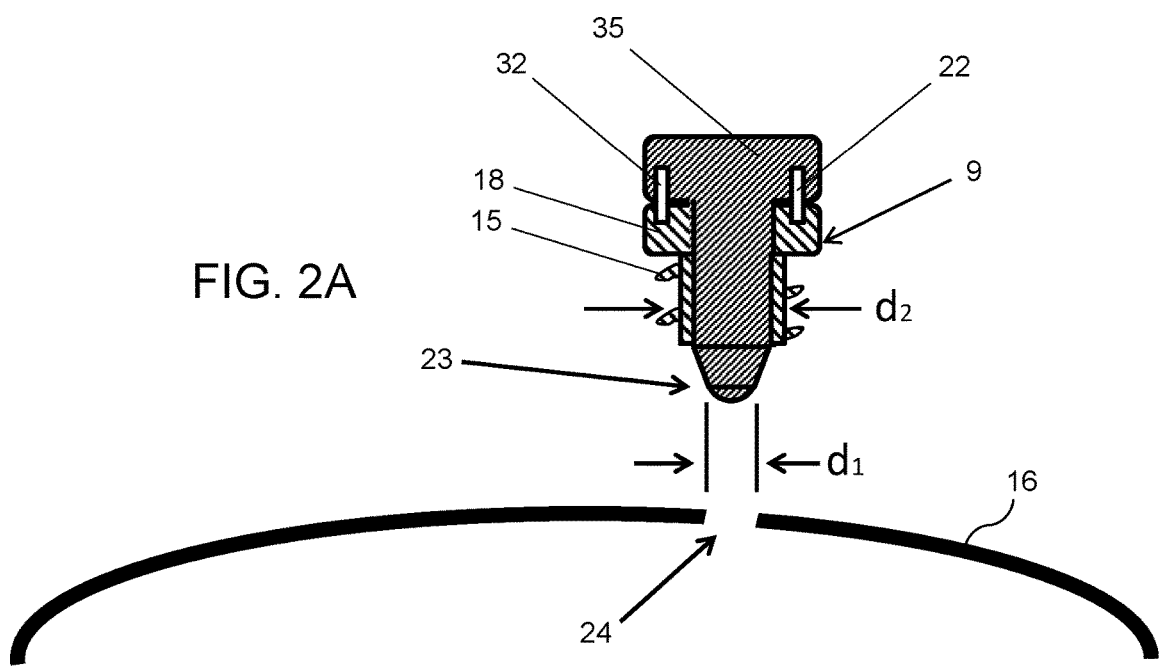
FIGS. 2A-2C depict a dilating port for accessing a body cavity through the skin.
Figure 2B:
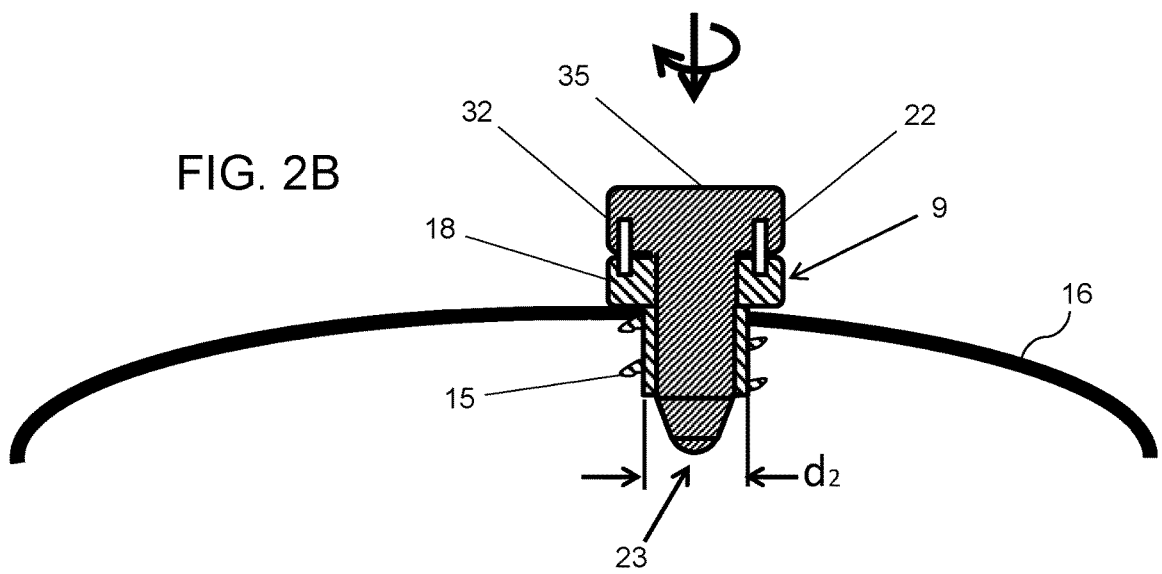
Figure 2C:
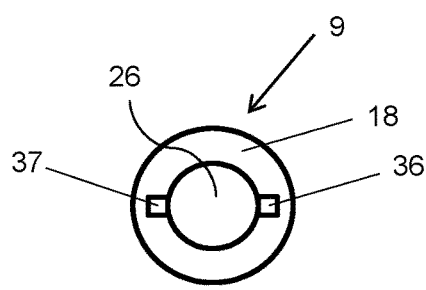

In order to perform laparoscopic surgery, access into the body is made through skin incisions. FIGS. 2A-C illustrate a dilating port 9 shown in a cross-sectional view; the port 9 is designed to maintain a skin incision 24 that is smaller than the objects that pass through the skin incision, that is, the skin incision 24, has a length of $d_1$ as shown in FIG. 2A, which may be smaller than the diameter $d_2$ of the dilating port 9.

In some embodiments, the dilating port 9 is an entry port that may have a deep, wide-pitched, continuous, or discontinuous thread 15 on its outer surface, and interface with an obturator 35 that may have a blunt tip 23 which may be conical and tapered at its distal end as shown in FIGS. 2A and 2B. The blunt tip enables the obturator 35 to pierce and spread skin 16, or any tissue, substantially atraumatically to introduce the dilating port 9. The dilating port 9 may engage with the obturator 35 through any engagement features known to one skilled in the art. For example, the top flange 18 of the dilating port 9 may contain a set of slots 36 and 37, as shown in FIG. 2C, extending axially that accept one or more matching pins 22 and 32 in the obturator 35. Hence, the dilating port 9 is pinned to the obturator 35, such that rotation of the obturator 35 rotates the dilating port 9 so that it may screw into the skin incision 24. It is within the scope of this disclosure that the engagement of the obturator 35 and the dilating port 9 may be accomplished by other features such as matching toothed profiles or corrugated surfaces, as long as the interface allows the obturator 35 to remain engaged to the dilating port 9 as the operator rotates the obturator 35, so that the obturator 35 drives the dilating port 9 through the skin incision 24. Furthermore, the operator may grasp either the first dilating port 9 or the obturator 35 to drive the assembly into the body once they are engaged. Multiple pairs of dilating ports 9 may be placed in the skin to provide multiple access points to deliver devices to reappose tissue such as in the case of a long ventral defect.

The assembly formed by the assembled obturator 35 and dilating port 9 dilates the skin incision 24 as it advances, resulting in the placement of a port with a diameter $d_2$ that may be much larger than the skin incision $d_1$; for example, $d_2$ may be approximately 2.5 times the length of $d_1$, enabling a larger device to be inserted into the body via a small skin incision. Due to the elasticity of the skin, the incision 24 returns substantially to its small initial size $d_1$ upon removal of the dilating port 9. Both the dilating port 9 and the obturator 35 may be formed of a metal or plastic material such as polycarbonate, PEEK, ABS, or stainless steel, and the pins 22 and 32 may be plastic or a metal such as stainless steel, or mating protrusions formed in the obturator 35 and/or dilating port 9.

It would be apparent by one skilled in the art that the systems and methods disclosed herein do not necessarily require ports. That is, the various devices disclosed may be inserted directly through incisions in the skin. In laparoscopic surgeries, the body is typically insufflated with a gas, so the various tools may have features to prevent the gas from leaking out such as seals. Alternatively, some of the devices may be inserted so quickly through the skin, such as the anchors, that significant gas would not leak out from the body, thus a seal may not be required.

Figure 3A:
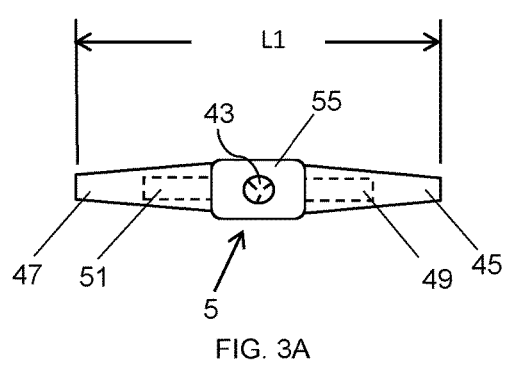
FIGS. 3A-3G illustrate various aspects of an anchor.
Figure 3B:
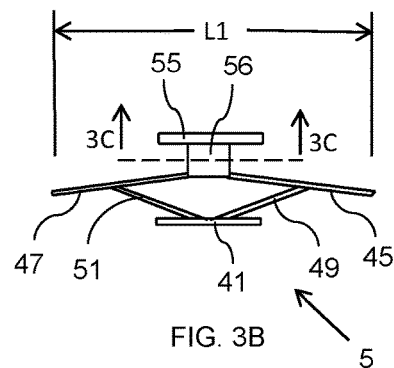

Now with reference to FIG. 3A which shows a top view of an embodiment of an anchor 5. FIGS. 3A-B show the device in its initial state, wherein it forms a substantially symmetrical, mostly collapsed, four bar linkage, with upper struts 45 and 47, lower struts 49 and 51, an upper flange 55, and a lower flange 41. The upper flange 55 may be engaged by the anchor delivery plunger 28 (FIG. 1), and the lower flange 41 may form an enlarged surface contact area upon placement onto the anterior rectus sheath 8 (FIG. 1) which spreads the force, thus reducing the pressure applied to the anterior rectus sheath 8. In its delivery state, as shown in FIG. 3D, the anchor 5 has been compressed to lengthen its vertical dimension L3 while minimizing its transverse dimension $L_2$ by virtue of the deformation of the anchor 5.

Devices exhibiting this type of mechanical action are similar to and commonly referred to as a toggle, expanding anchor, two-state mechanism, flexure, elastic hinge, living hinge, or toggle wing. The anchor 5 may be made from any suitable implantable material such as plastics like polypropylene that may act as an elastic hinge or other plastics or metals that may deform as an elastic hinge, or the anchor 5 may incorporate mechanical hinges such as pins or revolute joints to accomplish the hinging action. In the current embodiment, as shown in FIG. 3B, the deformable polymeric material of the anchor creates living hinges at the junction of the linkage members, for example where the lower struts 49 and 51 engage with the lower flange 41, and where the lower struts 49 and 51 engage the upper struts 45 and 47. Likewise, an elastic hinge is formed where the upper struts 45 and 47 engage the upper flange base 56. The anchor 5, may be symmetric as shown.

Figure 3C:
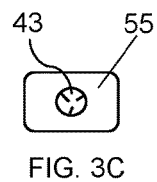
Figure 3D:
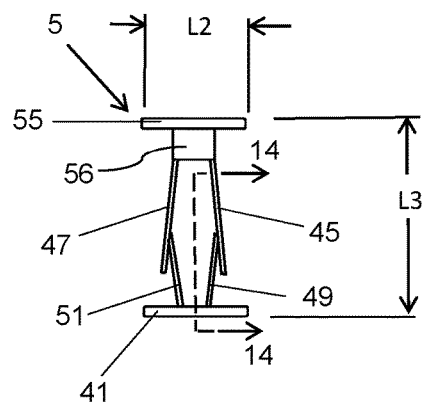
Figure 3E:
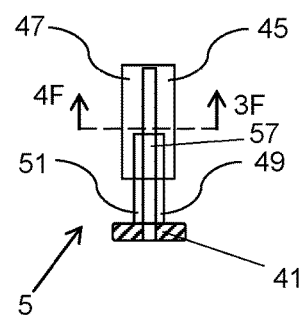
Figure 3F:
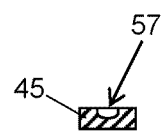
Figure 3G:
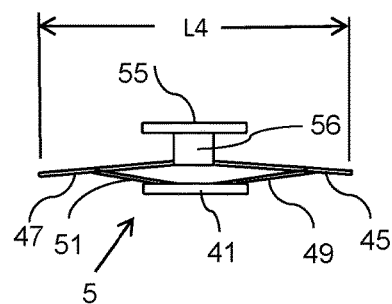

FIGS. 3A, 3B, 3D, and 3G illustrate how the anchor 5 may be actuated in practice. The anchor 5 may be initially manufactured in some intermediate state, that is, in between fully deployed and fully compressed as shown in FIGS. 3A and B; in this state the device may have an overall length span of $L_1$ between the tips of the device. When compressed for introduction into the dilating port 9 (FIG. 2) the device is reduced in width to $L_2$ which is substantially less than $L_1$, as shown in FIG. 3D. Finally, when the anchor 5 is deployed and compressed, its overall width $L_4$ may be equal to or larger than $L_1$ as shown in FIG. 3G. Hence, a large surface area will remain in contact with the anterior rectus sheath; the contacting surface includes at least the lower flange 41, but also may include the lower struts 49 and 51 and the ends of the upper struts 45 and 47 as the tissue deforms to seat against the anchor 5. The upper struts 45 and 47 may have an increased wall thickness compared with the lower struts 49 and 51, such that upon full deployment (FIG. 4G), the anchor resists folding in the backwards direction.

The anchor 5 may have grooves to maintain a central channel through the elongated anchor to accommodate passage of a needle while the anchor resides within the delivery device. For example, FIG. 3E shows a sectional view of the anchor 5 having a groove 57 in upper strut 45 and lower strut 49. FIG. 3F is a sectional view showing the groove 57 in upper strut 45. The second (opposite) side of the device may also have a similar groove to allow clearance for passage of a needle or strap.

As shown in FIG. 3A, a lock 43 may be located in the central channel immediately inferior, within, or on top of the upper flange 55, to lock a strap 12 (FIG. 2) as it exits through the anchor. FIG. 3C shows this lock 43 in a sectional view taken from FIG. 3B. The lock 43 is an aperture that may consist of a plurality of angled fingers molded into the central channel of the upper flange 55 for example. In further embodiments, the lock 43 may be a ratchet tab such as that used in zip ties or cable ties or any other mechanism that is designed to only allow passage of a strap in one direction while locking it from motion in the opposite direction such as an annulus that has teeth, prongs, or a cone aperture to allow a strap, which may be smooth or having engaging features, to pass in only one direction. As described in more detail below, this mechanism allows serial tensioning of the individual straps to close the abdominal wall defect without relying on sutures or clamps.

The above description of an anchor 5 is not meant to be in any way limiting, but only exemplar of one type of expanding anchor. One skilled in the art will appreciate that there are many devices that can be introduced in a compressed state with a smaller cross sectional area and expanding to a larger cross sectional area, such as toggles and drywall type anchors. These and other alternative expanding devices, such as those that may be round, spherical, or unsymmetrical are within the scope of this disclosure. Furthermore, the anchor need not expand per se, but it may be a substantially rigid structure capable of passing through a needle in a narrow direction with little or no flexing and then being reoriented inside the body to lay on the anterior muscle surface in a long direction, thus accomplishing the desired function of creating a relatively large footprint on the muscle so that the anchor is not able to pull through the tract in the muscle.

Figure 4:
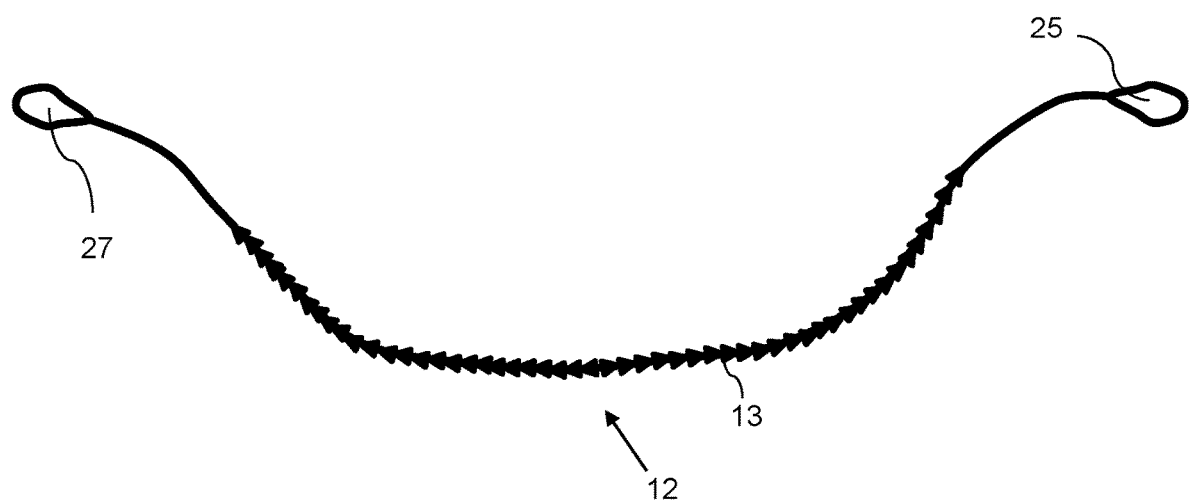
FIG. 4 depicts a ratchet strap.

Now with reference to FIG. 4, an embodiment of a strap 12 having barbs 13 that operatively engage with the lock 43 of the anchor 5 (FIG. 3C) to permit tensioning in one direction. For example, when the right strap loop 25 is pulled, the barbs 13 allow the strap 12 to travel in the direction of the right strap loop 25 while resisting travel backwards through the anchor 5. The strap may be comprised of any suitable materials such as molded plastic and the barb diameters may be, for example, approximately 1.8 mm or any size that allows engagement with the lock 43.

The description of the strap 12 is not meant to be in any way limiting but only exemplar of a one-way locking device. The strap may be flat or round, and it may have teeth on one or both sides or conical or cone shaped features encircling the strap. One skilled in the art will understand that there are many ways to make a strap/orifice combination such that the strap that passes in only one direction through the orifice. Indeed, the strap may be smooth such that it passes through the orifice in only one direction due to features on the orifice, such as flexing tabs or a tapered or conical shape.

Various embodiments of a method or technique and instrumentation to place multiple interrupted fastening loops on each side of a hernia defect and to maintain tension in each loop while allowing serial cinching of each loop to reappose the edges of the defect will now be disclosed. The procedures may be performed laparoscopically, via multiple small incisions and trocar ports. The order of steps described herein is for illustrative purposes only and is not intended to limit the scope of the invention, as various alternative combinations or permutations of the sequence of steps are contemplated.

Figure 5A:
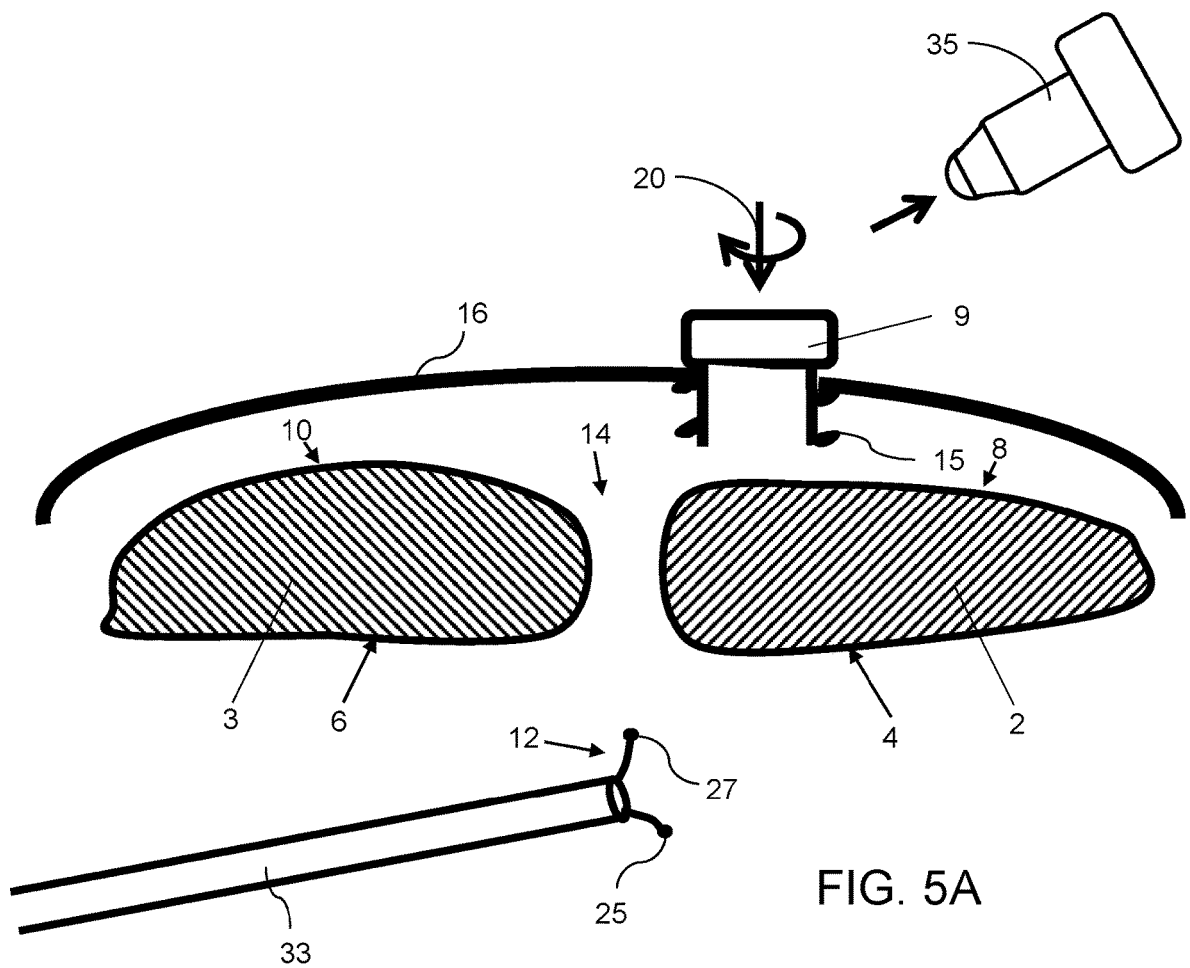
FIGS. 5A-5G illustrate a system and method for repairing a fascial opening.
Figure 5B:
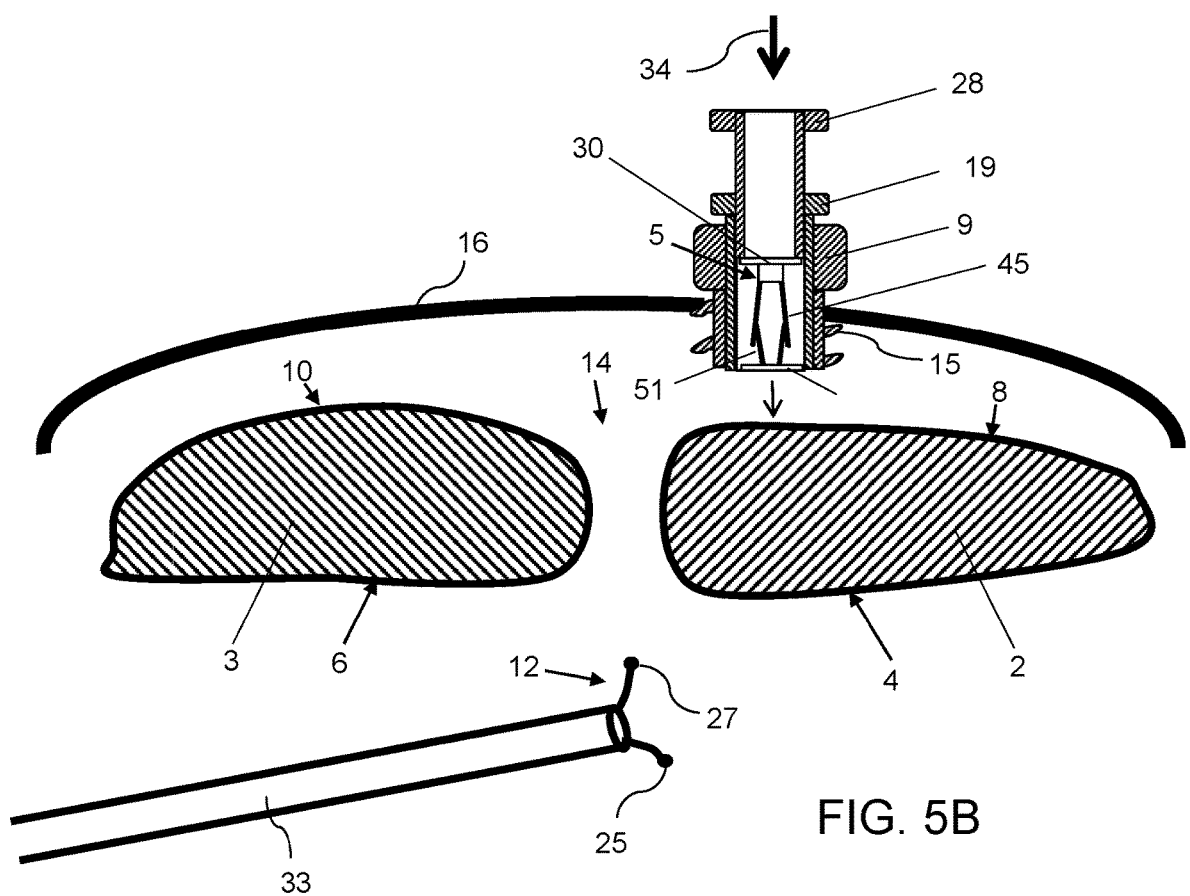

The proposed technique involves delivery of a barbed or ratcheted strap 12 into the abdominal cavity as shown in FIG. 5A; the strap 12 may be delivered through a strap introducer 33 which may be placed through a lateral access port into the body. As illustrated in FIG. 4, the strap 12 may include barbs 13 or similar ratchet teeth that point outwards oppositely on both sides towards the ends of the strap 12. As previously described and illustrated in FIGS. 2A and B, a dilating port 9 is inserted through the skin 16 through small skin incisions. After the obturator 35 drives the dilating port 9, as indicated by the rotating arrows, the obturator 35 may be removed from the dilating port 9, as shown in FIG. 5A, to allow access to the inner lumen of the dilating port 9. In FIG. 5B, the anchor 5 is shown being inserted into the lumen of the dilating port 9, the anchor 5 being in a narrow configuration that was previously described and illustrated in FIG. 3D. The anchor delivery plunger 28 slides inside of the delivery tube 19 engaging with the anchor 5 to push it through the dilating port 9 and into the body cavity when the operator applies a force to the anchor delivery plunger 28 in the direction indicated by the arrow 34. Multiple, spaced, expanding anchors may be placed via delivery tubes in this manner into the subcutaneous space on the surface of the right anterior rectus sheath 8 and left anterior rectus sheath 10.

Figure 5C:
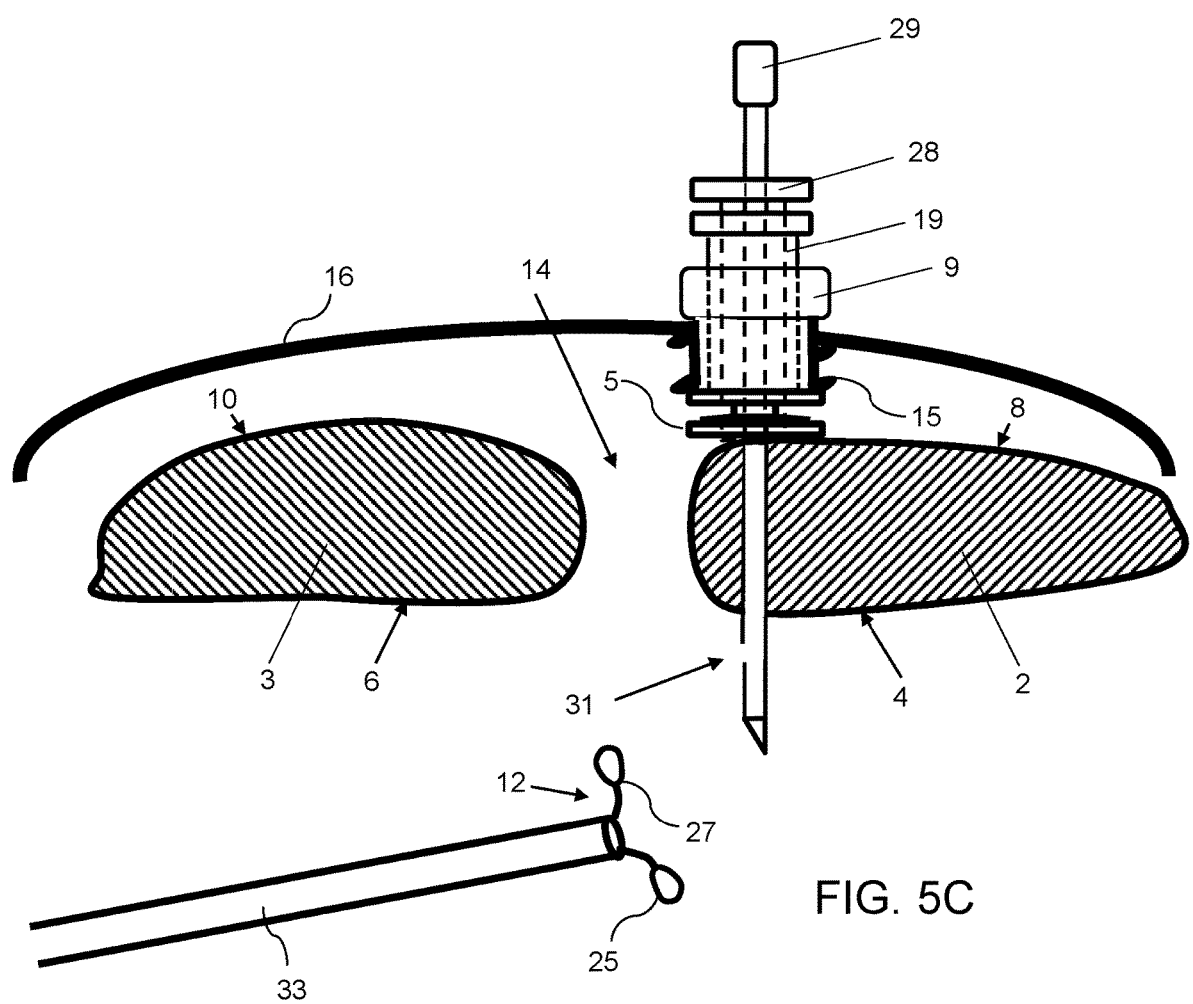
Figure 5D:
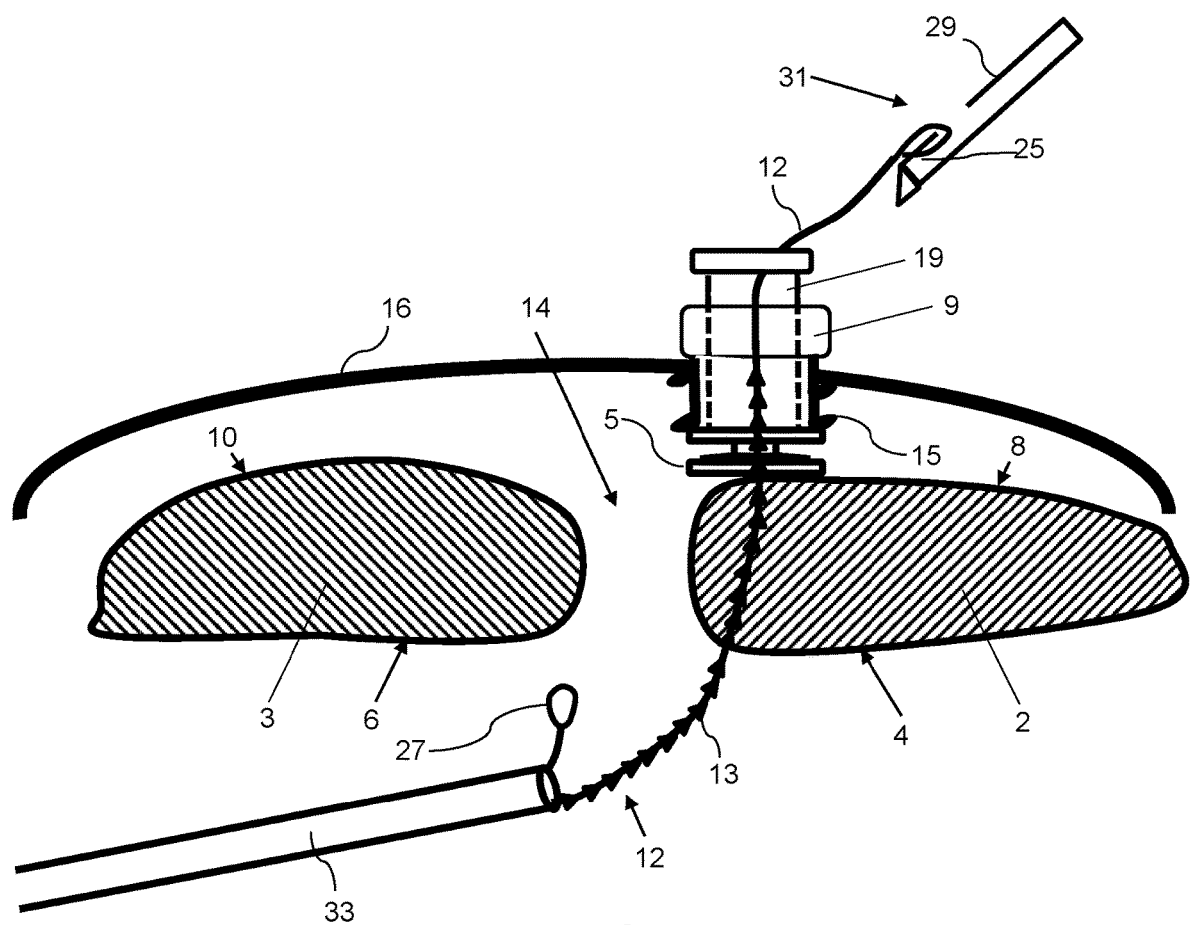

With reference to FIG. 5C, the anchor 5 is shown in its fully deployed state such that it rests upon the right anterior rectus sheath 8. A hook needle 29 is inserted through the delivery tube 19, the anchor delivery plunger 28, and through the central opening in the anchor 5. For example, the hook needle 29 may be placed through the anchor 5 before it is expanded, to hold the anchor 5 in place while it is expanded by the anchor delivery plunger 28, thus serving to automatically locate the anchor 5 over the hole in the right anterior rectus sheath 8 that the hook needle 29 creates. With the hook needle 29 placed through the full-thickness abdominal wall including through the right rectus abdominus 2, the strap loop 25 may be engaged by a feature such as a slot 31 on the hook needle 29 as shown in FIG. 5D and pulled through the right rectus abdominus 2, through the anchor 5, and out of the body.

The present embodiments illustrate that a large needle need not traverse through the rectus abdominus 2 to place the anchor of the proposed system onto the posterior anatomy, (e.g. the posterior rectus sheath 4) which would require a larger hole through the right rectus abdominus 2. In the present embodiments, the anchor is inserted directly onto the anterior rectus sheath 8, thus permitting the use of a small hook needle 29 to traverse through the rectus abdominus 2 in order to engage with the strap 12. The hook needle 29 (FIG. 5D), which may have an outer diameter of about 1 mm to 5 mm, or for example 2 mm, may be inserted through a small central hole in the anchor 5 and into the abdominal cavity, where it engages the strap loop 25 of the strap 12 and pulls the strap 12 through the full thickness abdominal wall (rectus abdominus 2) and through the lock 43 of the anchor 5. The strap 12 may have an outer diameter such that it fits inside the hook needle 29, for example 2 mm. The lock 43 may accommodate a larger diameter than the strap 12 passing through it, such as the hook needle 29 because the locking features (e.g. teeth, flexure, prongs, tapered section) may flex out of the way temporarily while the hook needle 29 is inserted while flexing back into the shape required to engage with the strap 12 once the hook needle 29 is withdrawn.

While a strap 12 with a larger diameter may reduce the likelihood of incising tissue, it would also require a larger hook needle 29 which increases the size of the puncture tract through the muscle tissue. The contact surface area of the anchor 5 in its expanded configuration is much larger than the puncture hole created by passage of the hook needle 29 and strap 12 through the rectus abdominus 2, diminishing the potential of anchor 5 pullout via the needle puncture tract. For example, for a needle with a diameter of 2 mm, its puncture hole would have an area of approximately 3 mm$^2$, while an anchor with a deployed footprint of 38 mm×8 mm would have a contact area that is approximately 300 mm$^2$ which is 100 times greater than the puncture hole.

It is within the scope of this disclosure that the slot 31 on the hook needle 29 may be any passive feature such as a slot, hook, or caribiner type latch, or an active grasping mechanism such as a claw, jaw, or clasp. Furthermore, the hook needle 29 may be in elongate member such as a tube or hypotube with or without a bevel that is capable of passing through the muscle tissue through an existing hole or by creating a hole as it is advanced into the body cavity. All of which may allow the strap loop 25 to be grasped and retrieved out of the abdominal cavity.

Figure 5E:
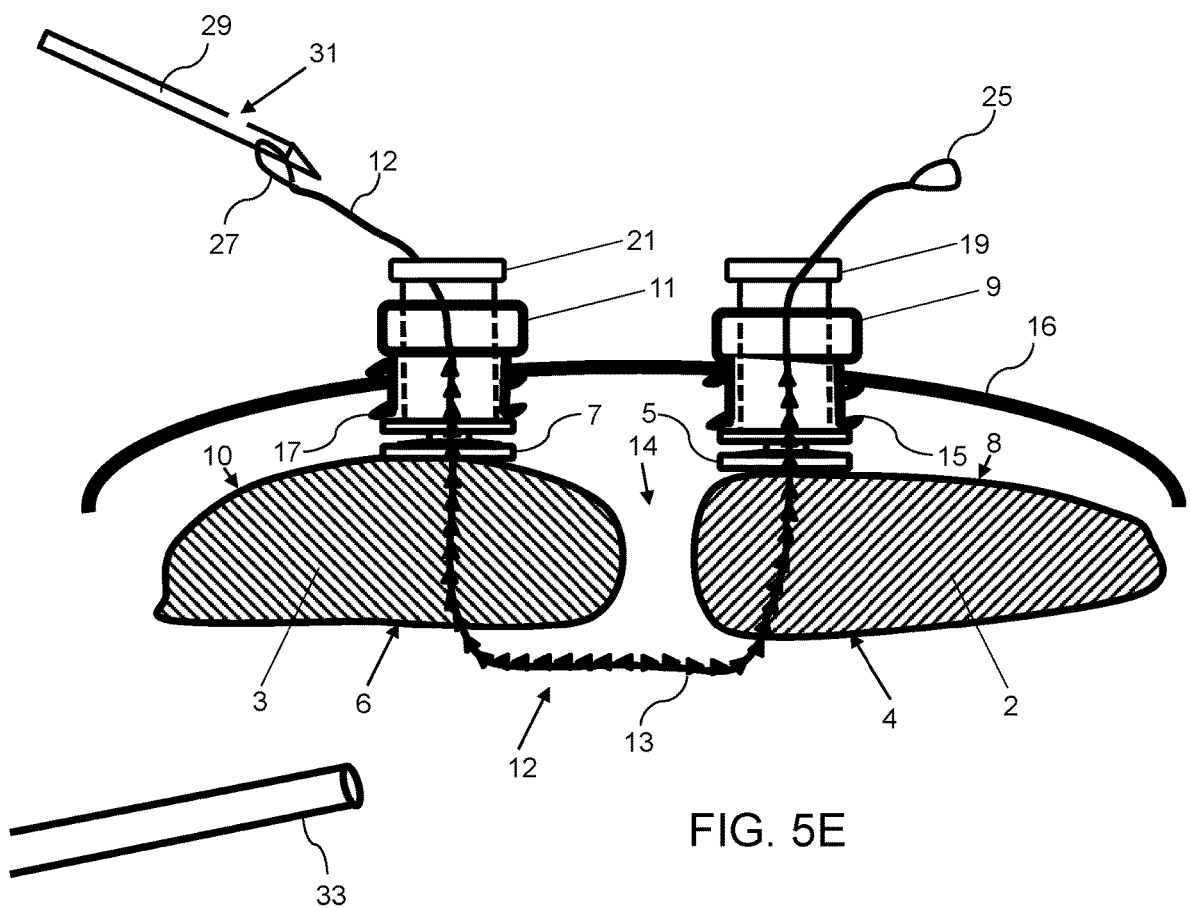

The same procedure described above regarding delivery and expansion of the anchor 5 may be conducted on the contralateral side as shown in FIG. 5E, to install another anchor 7, dilation port 11, and delivery tube 21 in place. With the hook needle 29 placed through the left rectus abdominus 3, the strap loop 27 may be engaged by the slot 31 on the hook needle 29 and pulled through the delivery tube 21. With the strap 12 bridging across the fascial opening 14, the system is primed for tensioning of the strap 12 to approximate the right and left rectus abdominus 2 and 3 along the length of the defect. In general, the arrangement shown in FIG. 5E may be duplicated longitudinally along the abdomen along the length of the hernia defect so that there may be multiple pairs of ports, anchors, and concomitant straps residing through the skin and muscle, after which they may be serially tensioned with multiple passes to gradually approximate the right and left rectus abdominus 2 and 3. The longitudinal distance between anchor pairs may be approximately 2 cm or any other distance that allows the defect to be fully closed. The locking anchors 5 and 7 prevent the strap 12 from loosening while the surgeon performs serial tensioning of other anchor pairs that have been placed.

Figure 5F:
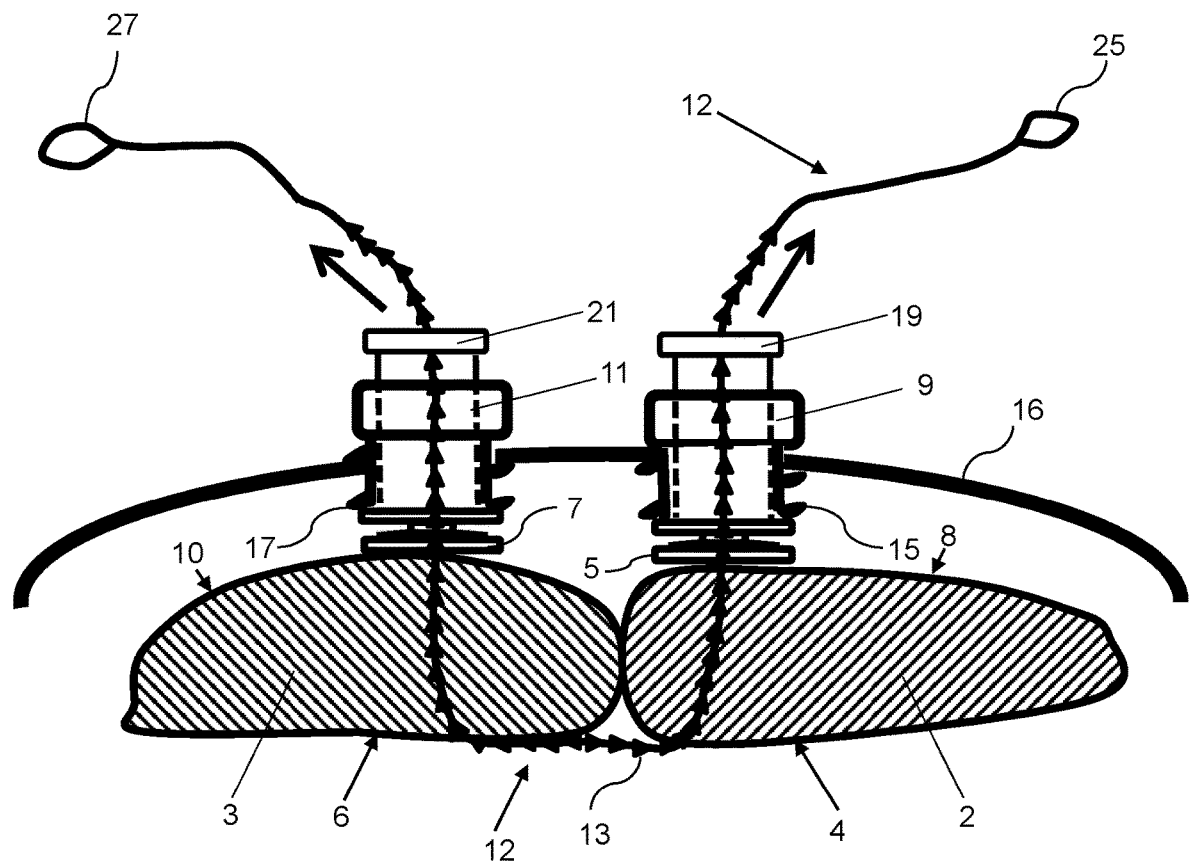

FIG. 5F shows a strap 12 being pulled (arrows) such that it is fully tensioned and the right and left rectus abdominus 2 and 3 have been reapposed as the defect has been repaired. During the tensioning process, each delivery tube 19 and 21 may be maintained in position within the dilating ports 9 and 11 so that the surgeon may apply counter-traction to the anchors 5 and 7 respectively upon strap 12 withdrawal. Alternatively, the dilating ports 9 and 11 may be used to apply counter-traction to the anchors 5 and 7 if the anchor is wider than the dilating port.

Figure 5G:
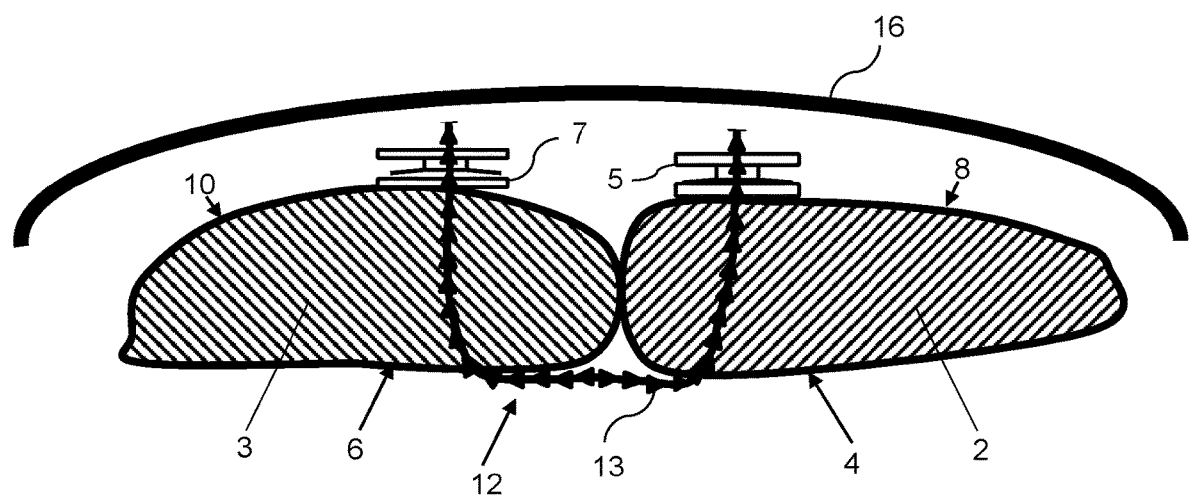

As shown in FIG. 5G, the dilating ports (not shown) have been removed and excess strap length has been cut near its exit from the anchor, leaving behind nothing on top of the skin 16 as the anchors 5 and 7 reside on top of the right and left anterior rectus sheaths 8 and 10.

The proposed embodiments of this application are simple and less tedious than other techniques. Furthermore, the system also provides the high degree of tension required to close a full thickness abdominal wall defect. This is a result of the insertion and placement of a large anchor onto the anterior abdominal wall through an incision in the skin of the patient, rather than piercing through the abdominal wall from inside the abdominal cavity, as in other laparoscopic surgical techniques. In the present embodiments, the anchors 5 and 7 do not pierce through to the posterior rectus sheaths 4 and 6, and no significant tract is formed whereby the anchors 5 and 7 may pull back through the anterior rectus sheaths 8 and 10. This reduces the likelihood of failure of the defect closure; the tract through the rectus muscles may be as small as the needle and/or strap. Furthermore, one skilled in the art would understand that the strap may be sized large enough in diameter to hold the required tension and to resist cutting through tissue as compared to a relatively thin suture, yet small enough to fit through a needle in order to pierce the muscle. Similarly, the anchors may be small enough to be introduced through ports or incisions in the skin, yet large enough to provide a footprint of contact on the anterior portion of the muscle so as not to incise into the tissue or into the tract that has been formed by the needle after the strap is tightened. Hence, in all of the embodiments disclosed herein, the anchors may alternatively be fixed in size and rather than expandable.

Figure 6A:
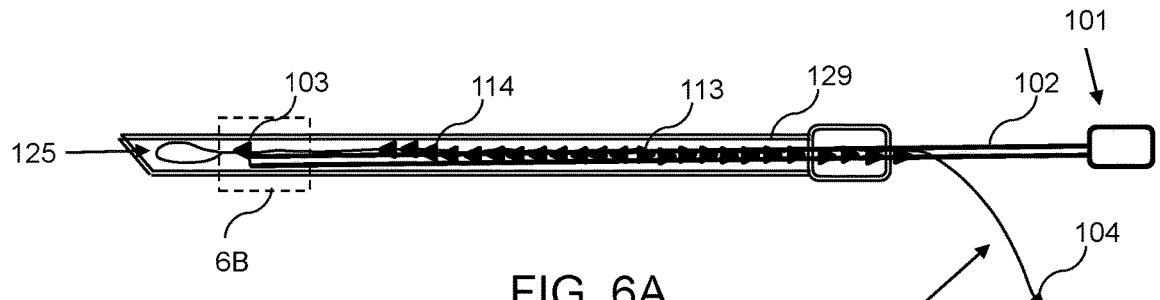
FIGS. 6A-6C illustrate a needle arrangement that houses a strap and stylet
Figure 6B:
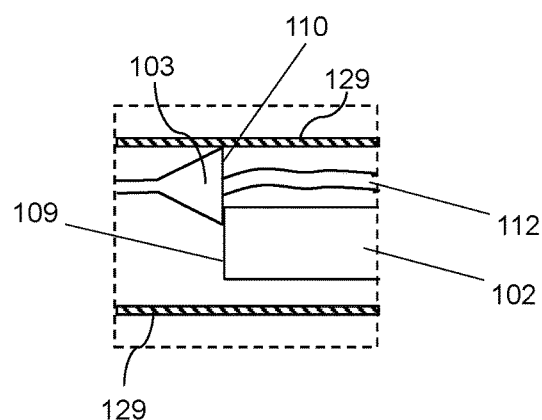
Figure 6C:
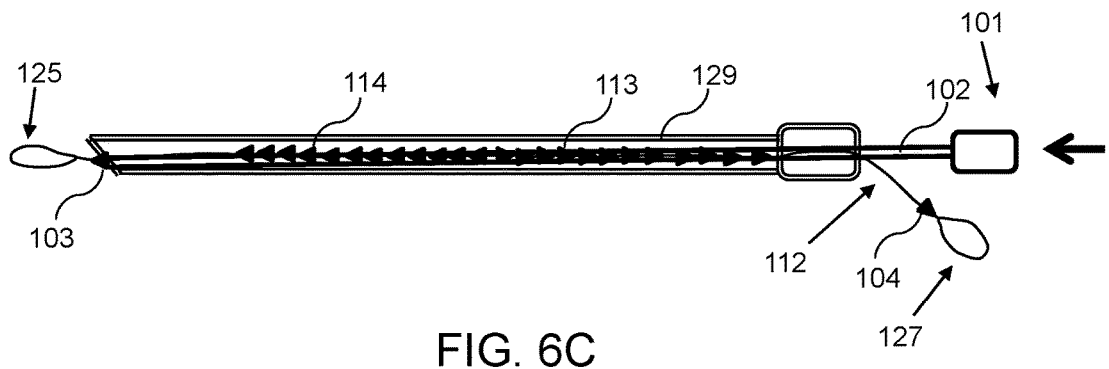

In yet another embodiment, an alternative technique for introducing the barbed strap into the abdominal cavity will be disclosed herein. With reference to FIGS. 6A-6C, a delivery needle 129 is shown with a strap 112 inside the lumen of the delivery needle 129 and a stylet 101, also residing inside the delivery needle 129 adjacent to the strap 112. The strap 112 and stylet 101 may be placed into the delivery needle 129 preoperatively or intraoperatively. The stylet 101 is used to advance the strap 112 out of the delivery needle 129 following needle insertion into the abdomen. Since the strap 112 may have insufficient column strength to be advanced out of the needle by being pushed at the proximal end of the needle, the stylet 101, having a long, relatively rigid rod 102, serves as a driver to advance the strap 112 out of the delivery needle 129. One skilled in the art would realize that there are many ways to drive the strap 112. By way of non-limiting example, the driving force may be imparted from the rod 102 to the strap 112 by friction due to the rod 102 being adjacent to the strap 112 within the relatively small needle, or the rod 102 may have features at its distal tip or along the rod 102 to engage with barbs 113 and 114 on the strap 112, or the rod 102 may engage a distal barb 103 with its distal end 109. The latter configuration is illustrated in FIG. 6B which is a partial view showing the engagement of the rod 102 with the barb 103.

With reference to FIG. 6A, the strap 112 comprises a barb 103 that lies proximal to the strap loop 125. As illustrated in FIG. 6B, the proximal face 110 of the barb acts as a structure for the distal end 109 of the rod 102 to exert push force when the operator pushes on the stylet 101. This causes the strap loop 125 to exit the lumen of the delivery needle 129, as shown in FIG. 6C so that it may be grasped by instruments within the body cavity.

Figure 7A:
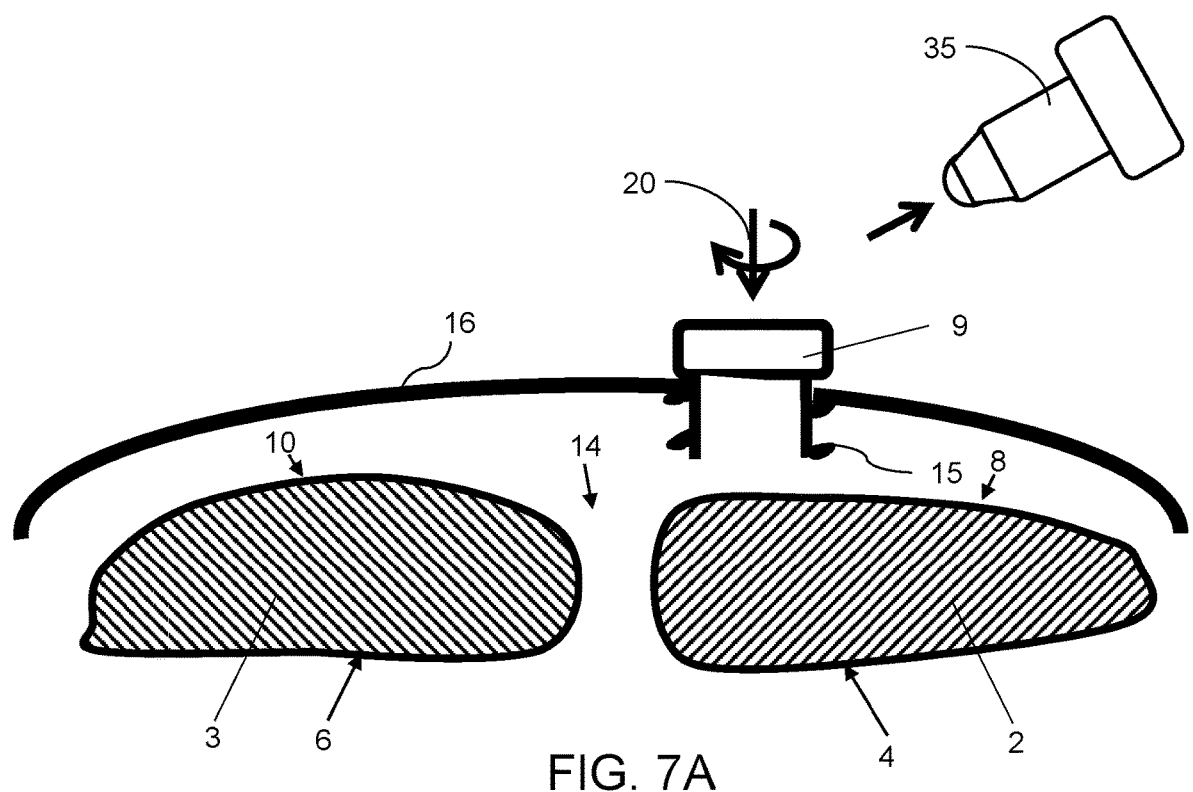
FIGS. 7A-7I illustrate another system and method for repairing a fascial opening.
Figure 7B:
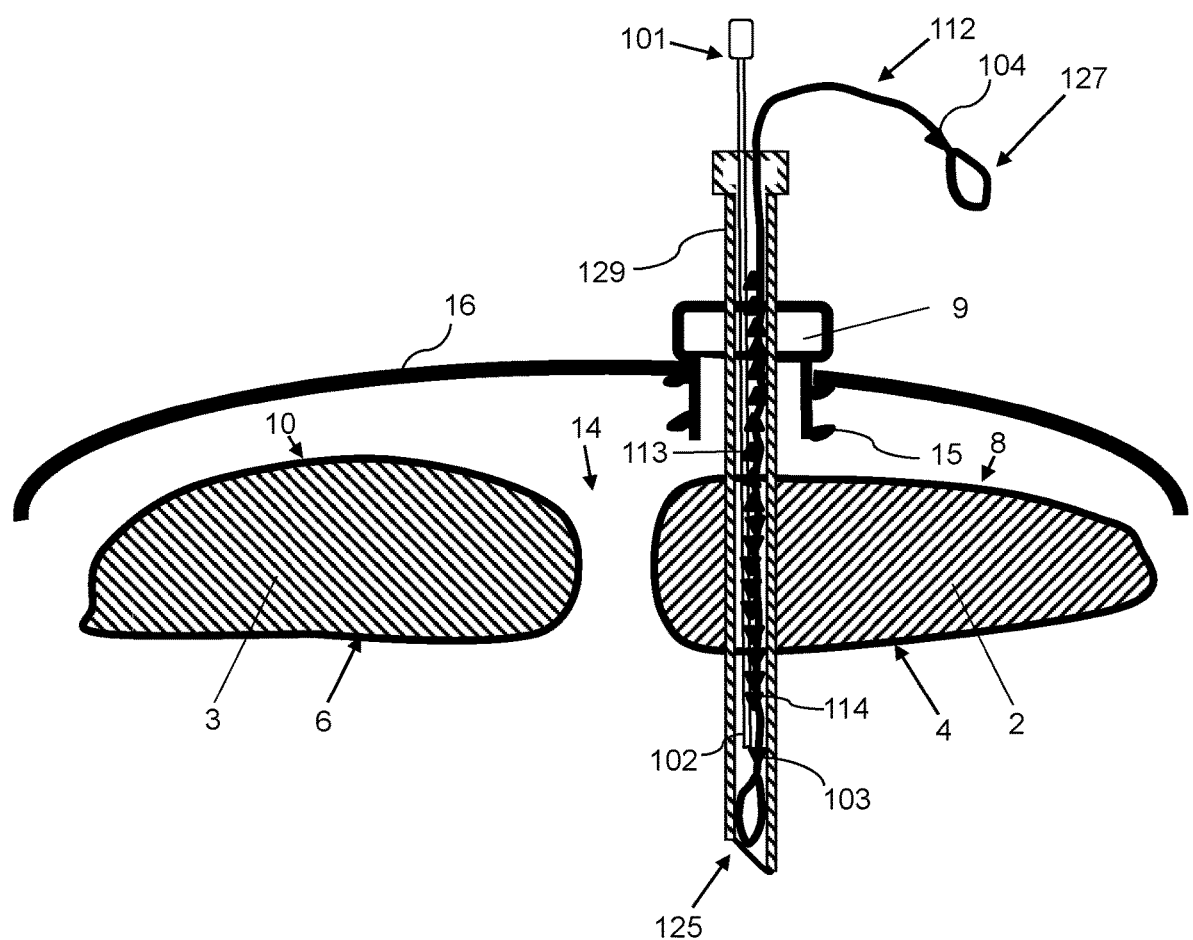
Figure 7C:
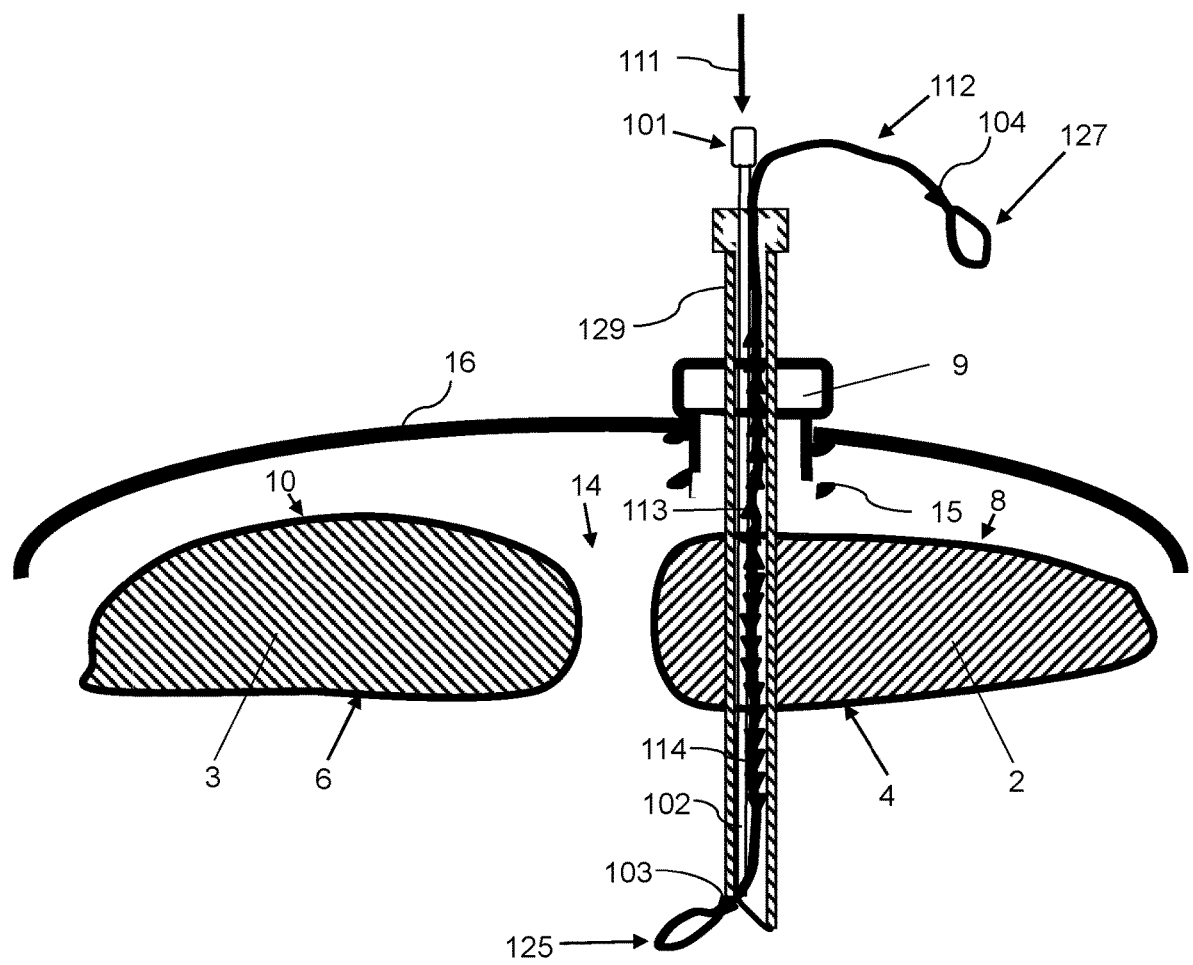

FIGS. 7A-7I illustrate an embodiment of a system and method for reducing a ventral hernia. As shown in FIG. 7A, one or both skin ports are placed through the skin providing access to the right or left anterior rectus sheath 8 and 6 similar to the step previously described and illustrated in FIG. 5A of this disclosure. However, instead of inserting the entire strap with both looped ends into the abdomen through a separate port, as shown in FIGS. 5B-5C, one strap loop 125 of the strap 112 is placed within the bore of a delivery needle 129 as shown in FIG. 6A. The delivery needle 129 may be of any length or diameter that is suitable for the procedure and for ventral hernia procedures the diameter is approximately 2-4 mm. The delivery needle 129 containing one end of the strap 112 is inserted into a dilating port 9, through the full right rectus abdominus, and into the abdominal cavity as shown in FIG. 7B. The stylet 101 is advanced distally as indicated by the arrow 111 in FIG. 7C such that the rod 102 drives the strap loop 125 out of the delivery needle 129, thus making the strap loop 125 accessible to any other instrument inside the body cavity to pull it in further.

Figure 7D:
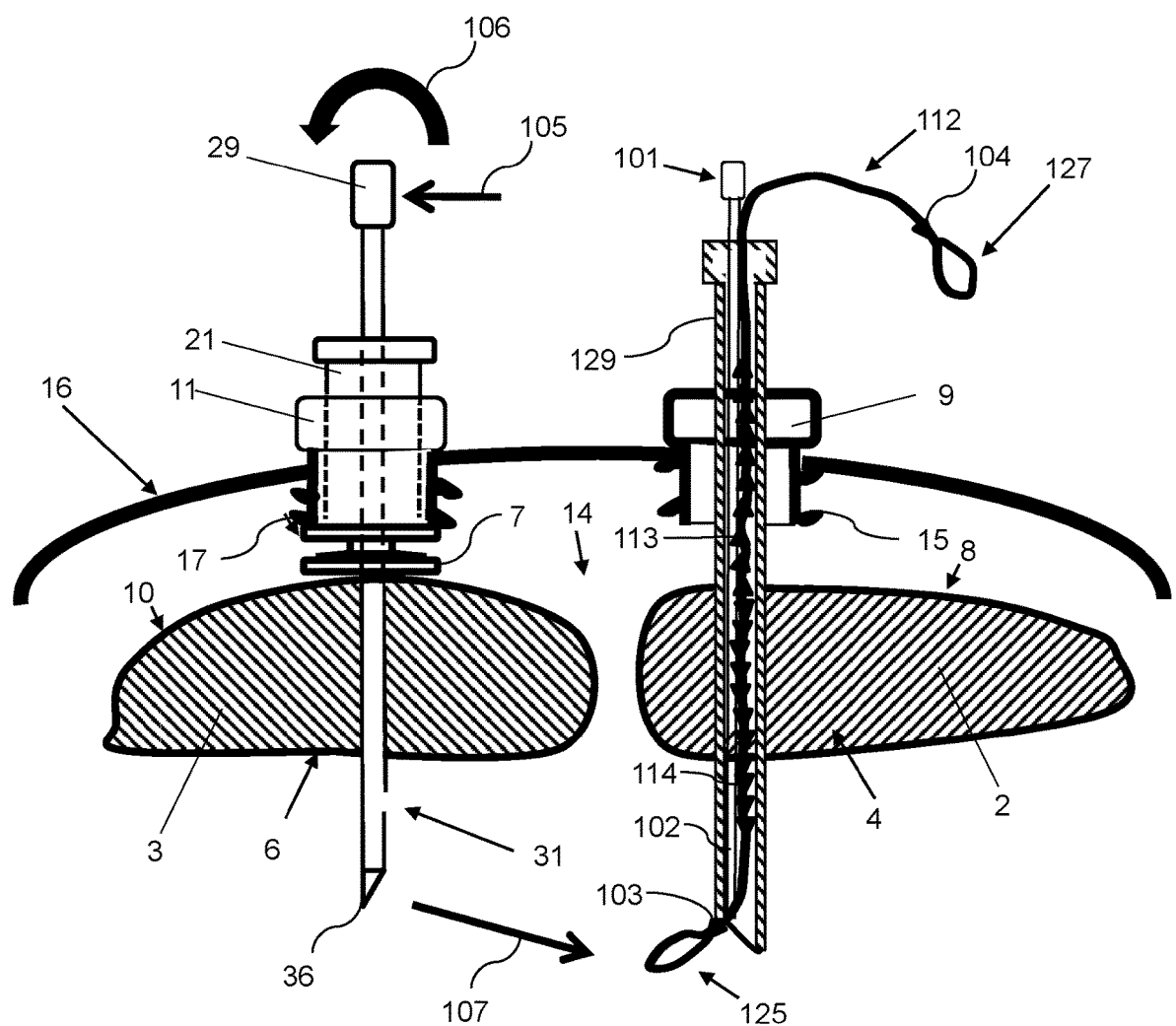

To pull the strap loop 125 into the body further, the contralateral side of the defect 14 is accessed as show in FIG. 7D. The dilating port 11 and anchor 7 are delivered in a similar fashion as that disclosed previously in this disclosure and illustrated in FIG. 7B, that is, the anchor 7 is delivered to the anterior rectus sheath 10 via the contralateral skin port. This contralateral access may alternatively be conducted before the needle 29 has been introduced into the abdominal cavity so that the contralateral side is prepared slightly in advance. In fact, one skilled in the art may prefer to perform the procedural steps disclosed herein in a different order due to, for example, surgeon preference or convenience and these modifications are within the scope of this disclosure.

Figure 7E:
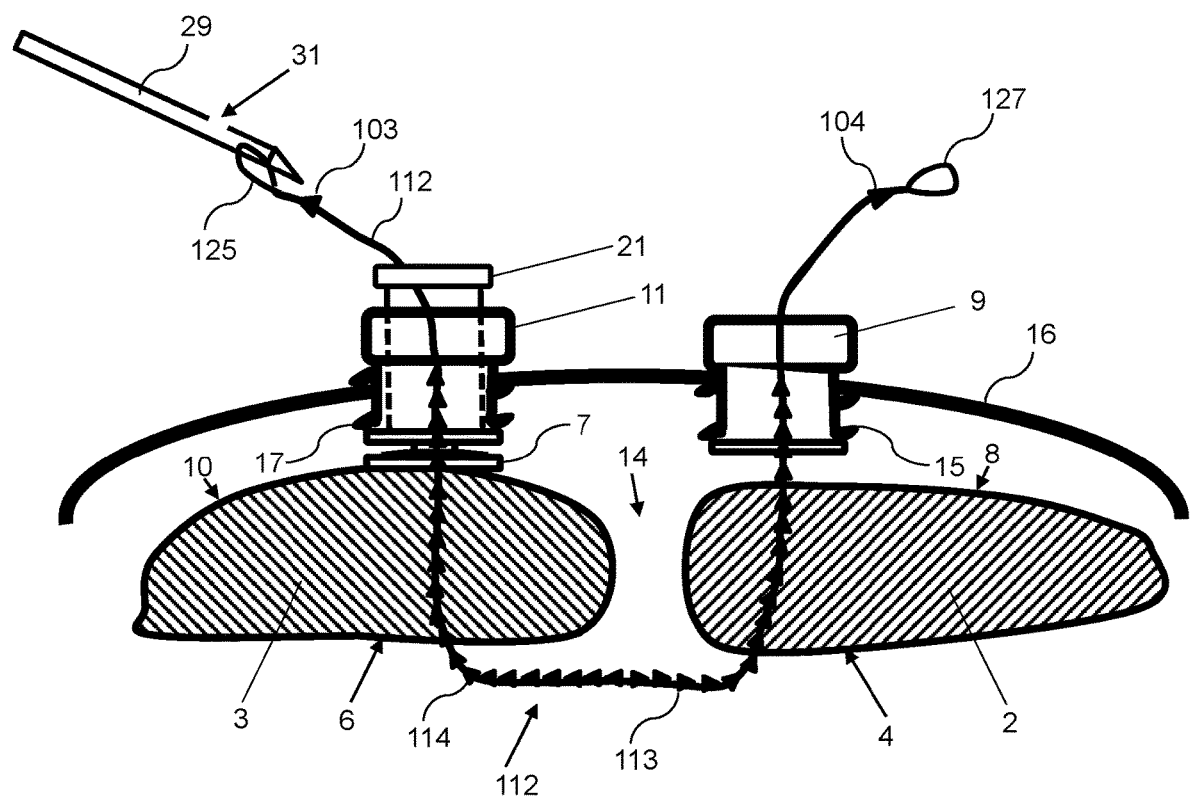

Next, the hook needle 29 is inserted through the dilating port 11, which may house the delivery tube 21, and through the anchor 7 and rectus abdominus 3 to grasp the strap loop 125 introduced by the delivery needle 129 through the port 9. This maneuver may be accomplished by manipulating the distal tip of the hook needle 29 by twisting in the direction of the arrow 106 or forcing the hook needle 29 as indicated by the arrow 107 such that the distal tip 36 moves toward the strap loop 125, as indicated by the arrow 107; this allows the slot 31, or other engagement feature, to engage with the strap loop 125. This maneuver is possible because the abdominal wall is relatively compliant, allowing access ports to be manipulated especially by twisting the inserted instruments. Likewise, the delivery needle 129 may be twisted such that the loop strap 125 moves closer to the distal tip 36 of the hook needle 29. As shown in FIG. 7E, the strap 112 may be pulled through the anchor 7 by the hook needle 29 while the aforementioned one-way ratchet mechanism in the anchor 7 secures the strap 112 from being pulled backwards into the abdomen. The delivery needle 129 (not shown) may be removed from the dilating port 11 leaving behind the strap 112. While the strap 112 is being pulled through the anchor 7, the resistance that may be imparted by the lock (see FIGS. 3A-3F) may be reacted by the operator pressing on the delivery tube 21 or the anchor delivery plunger 28 (not shown) which may also be in place during this part of the procedure.

Figure 7F:
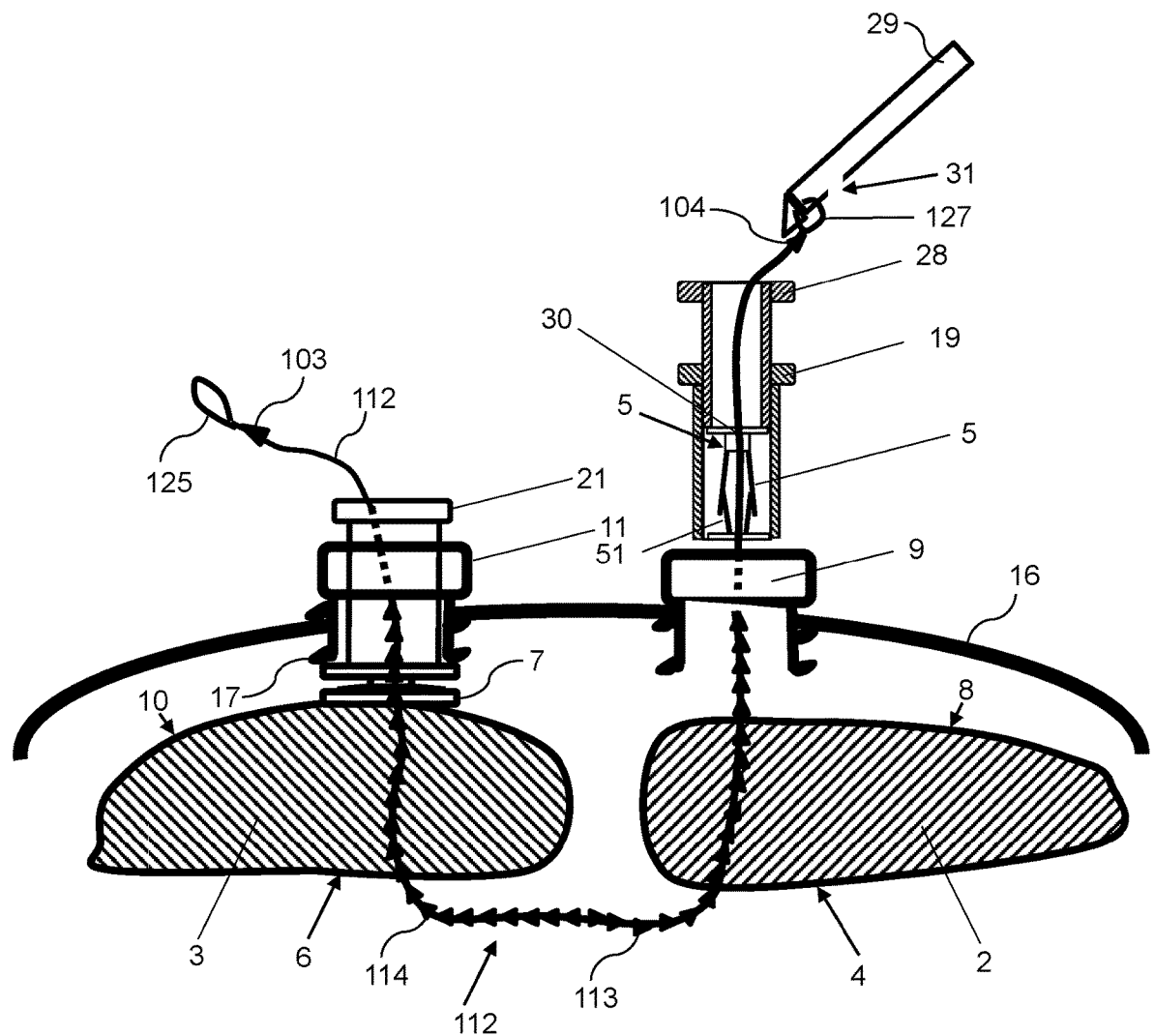
Figure 7G:
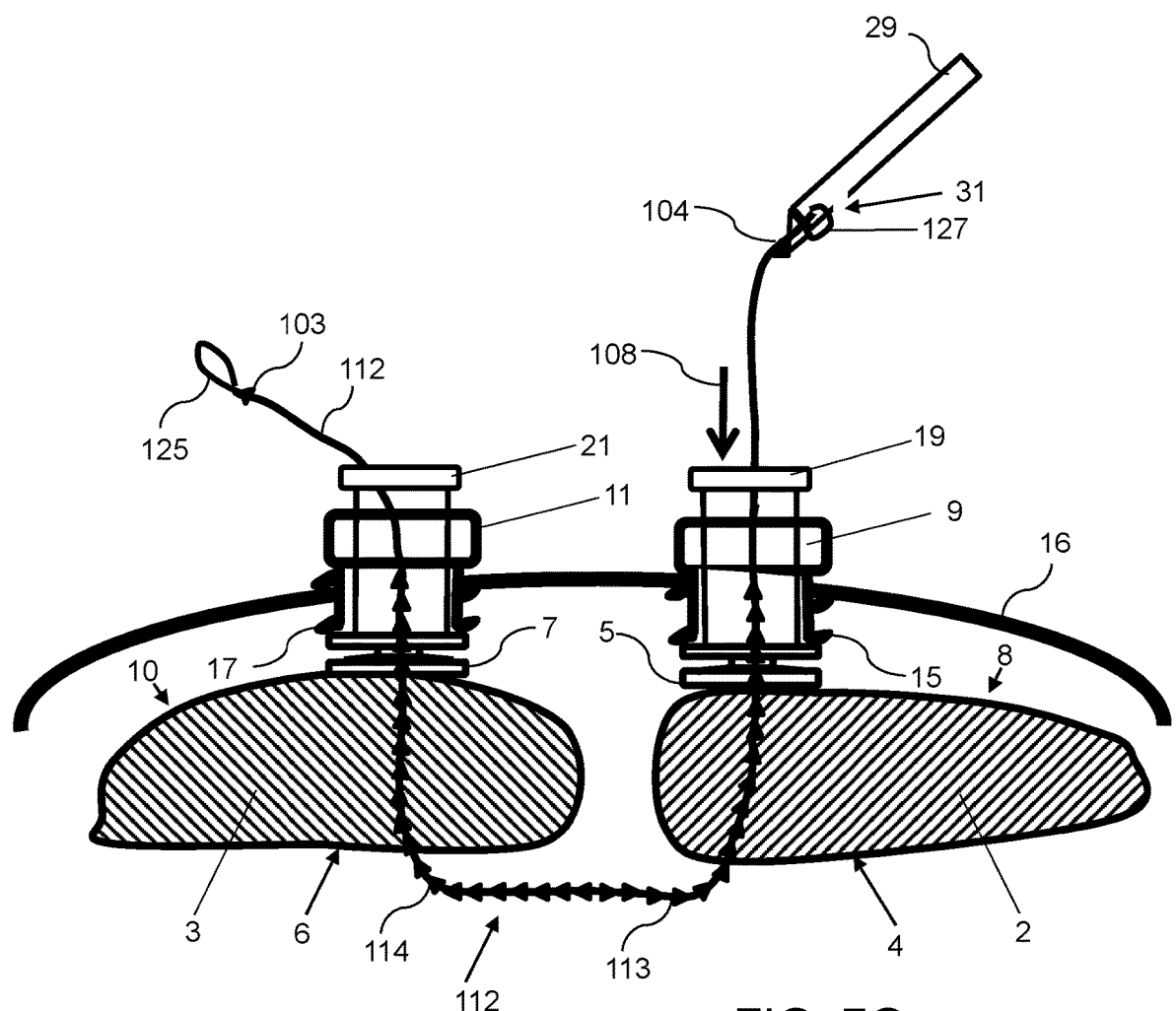
Figure 7H:
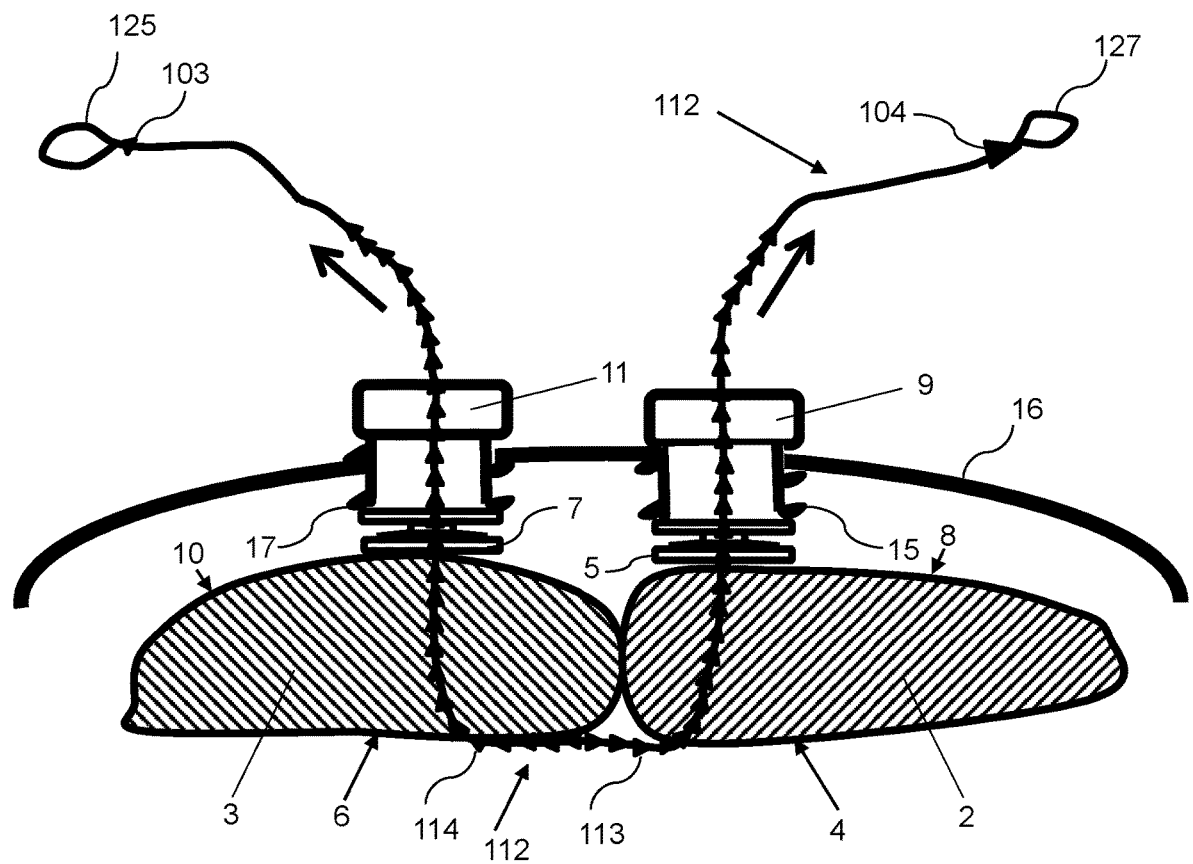
Figure 7I:
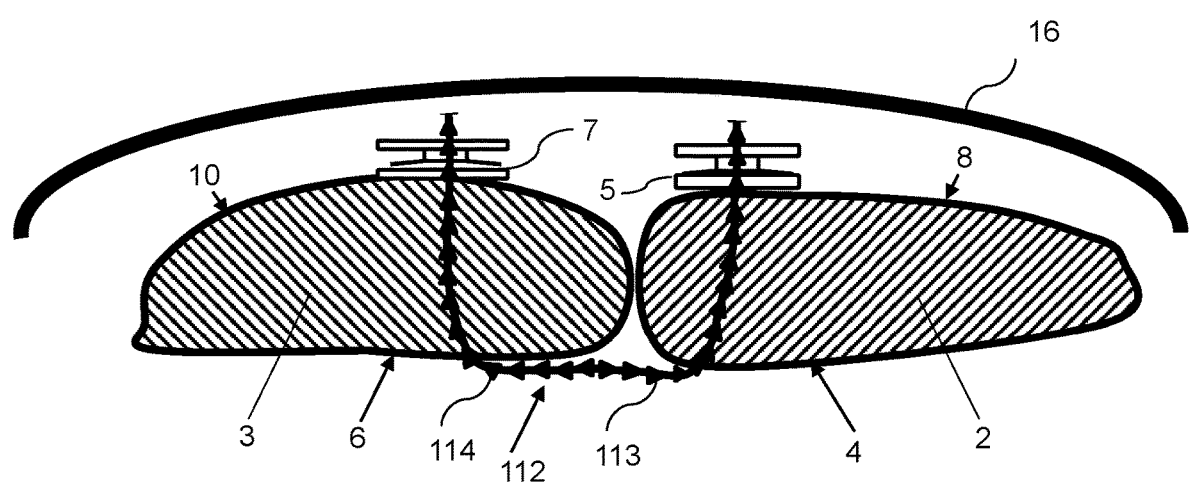

Now with reference to FIG. 7F, the anchor 5 on the opposite side is deployed. The strap loop 127 exiting the port 9 is grasped by the hook needle 29 inserted through the anchor 5; this is performed outside of the patient's body as the strap loop 127 already resides outside of the body. As shown in FIG. 7F, the strap 112 is pulled through the anchor 5 and the anchor 5 is advanced through the port 9 via the delivery tube 19, while optionally being pushed by the anchor delivery plunger 28. FIG. 7G shows the anchor 9 deployed onto the right anterior rectus sheath 8 wherein a force 108 may be applied to the delivery tube 19 to hold the anchor 9 in place while tensioning begins. Both ends of the strap 125 and 129 may be tensioned as indicated by the arrows in FIG. 7H to close the defect, prior to transection of the excess strap length outside the anchors as shown in FIG. 7I.

This embodiment does not require introduction of a large diameter strap introducer 33 through another port in the body, as shown in FIG. 5A. That is, his strap introducer 33 requires its own trocar port for insertion into the abdominal cavity. Instead, a single strand of strap 112 may reside inside of a delivery needle 129 that is inserted through one of the existing skin ports, as shown in FIG. 7B. This method also allows the operator to pull one end of the strap 112 through the anchor 5 outside of the patient's body, avoiding the laparoscopic coordination required to grasp both anchor loops 125 and 127 inside the abdomen.

A system and method for closing a fascial opening are described herein. While the present disclosure describes the system and method in the context of hernia repair, and in particular ventral hernia repair, the devices and methods presently disclosed may be used in any surgical procedure for joining tissue, closing an opening, or fastening a device to or between two or more sections of tissue. Additionally, while the current disclosure describes a method in the context of laparoscopic surgery, the method may be applied to any other class of procedure such as open surgery or laparotomy. The presently disclosed embodiments may also be operated or performed robotically with robotic manipulators working inside and/or outside of the body to manipulate the various devices. The robotic system may also actuate various aspects at the same time, for example, tightening multiple straps at the same time to approximate the defect in parallel rather than serially and measuring and reading out the tension force pulling on the strap. Furthermore, the presently disclosed systems and methods may optionally incorporate a hernia mesh similar to those used in typical hernia repair procedures or any new mesh systems or methods of application that may arise.

While this invention has been particularly shown and described with references to example embodiments thereof, it will be understood by those skilled in the art that various changes in form and details may be made therein without departing from the scope of the invention encompassed by the appended claims. While the above is a complete description of the certain embodiments of the invention, various alternatives, modifications, and equivalents may be used. The various features of the embodiments disclosed herein may be combined or substituted with one another. Therefore, the above description should not be taken as limiting in scope of the invention which is defined by the appended claims.

What is claimed is:

1. A method for closing a defect, the method comprising the steps of:
   inserting a delivery needle through a first opening in a body and through a posterior side of a first muscle;
   inserting a first end of a strap into the body through the delivery needle;
   placing a first anchor through a second opening in the body on an opposing side of the defect and onto an anterior surface of an opposing muscle;
   inserting a hook needle through the first anchor, and through the opposing muscle;
   engaging the strap with the hook needle;
   pulling the first end of the strap out of the body;
   inserting a second anchor over a second end of the strap and onto an anterior surface of the first muscle;
   pulling on the first and second ends of the strap to close the defect; and
   expanding the first and second anchors to a footprint larger than a diameter of the delivery needle.

2. A method for closing a defect, the method comprising the steps of:
   inserting a delivery needle through a first opening in a body and through a posterior side of a first muscle;
   inserting a first end of a strap into the body through the delivery needle;
   placing a first anchor through a second opening in the body on an opposing side of the defect and onto an anterior surface of an opposing muscle;
   inserting a hook needle through the first anchor, and through the opposing muscle;
   engaging the strap with the hook needle;
   pulling the first end of the strap out of the body;
   inserting a second anchor over a second end of the strap and onto an anterior surface of the first muscle;
   pulling on the first and second ends of the strap to close the defect; and
   expanding each anchor by pressing on a top of the anchor with a tube while pulling the strap through the anchor.

* * * * *